United States Patent
Ong et al.

(10) Patent No.: US 7,402,681 B2
(45) Date of Patent: Jul. 22, 2008

(54) COMPOUND WITH INDOLOCARBAZOLE MOIETIES AND DEVICES CONTAINING SUCH COMPOUND

(75) Inventors: Beng S. Ong, Mississauga (CA); Yu Qi, Oakville (CA); Yiliang Wu, Mississauga (CA); Yuning Li, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 142 days.

(21) Appl. No.: 11/167,512

(22) Filed: Jun. 27, 2005

(65) Prior Publication Data
US 2006/0214155 A1 Sep. 28, 2006

Related U.S. Application Data

(63) Continuation-in-part of application No. 11/011,678, filed on Dec. 14, 2004.

(51) Int. Cl.
*C07D 209/14* (2006.01)
*C07D 209/56* (2006.01)

(52) U.S. Cl. .................... 548/417; 548/418
(58) Field of Classification Search ................ 548/417, 548/418
See application file for complete search history.

(56) References Cited

U.S. PATENT DOCUMENTS

| | | | |
|---|---|---|---|
| 5,843,607 | A | 12/1998 | Hu et al. |
| 5,942,340 | A | 8/1999 | Hu et al. |
| 5,952,115 | A | 9/1999 | Hu et al. |
| 2002/0180349 | A1 | 12/2002 | Aziz et al. |
| 2004/0137271 | A1 | 7/2004 | Sohn et al. |

FOREIGN PATENT DOCUMENTS

| | | | |
|---|---|---|---|
| EP | 0 906 948 A1 * | 4/1999 | |
| EP | 0 908 787 B1 | 4/1999 | |

OTHER PUBLICATIONS

Submitted to applicant with NF of Jul. 11, 2007 in U.S. Appl. No. 11/167,485.*
Yuning Li et al., U.S. Appl. No. 11/011,901, filed Dec. 14, 2004, titled "Process to Form Compound With Indolocarbazole Moieties."
Christos D. Dimitrakopoulos et al., "Organic Thin Film Transistors for Large Area Electronics," *Adv. Mater.*, vol. 14, No. 2, pp. 99-117 (2002).
Salem Wakim et al., "Organic Microelectronics: Design, Synthesis, and Characterization of 6,12-Dimethylindolo[3,2-b]Carbazoles," *Chem. Mater.* vol. 16, No. 23, pp. 4386-4388 (published on web Jul. 7, 2004).
Nan-Xing Hu et al., "5-11-Dihydro-5,11-di-1-naphthylindolo[3,2-b]carbazole: Atropisomerism in a Novel Hole-Transport Molecule for Organic Light-Emitting Diodes," *J. Am. Chem. Soc.*, vol. 121, pp. 5097-5097 (1999).
Yiliang Wu et al., "Indolo[3,2-*b*]carbazole-Based Thin-Film Transistors with High Mobility and Stability," *Journal of the American Chemical Society*, vol. 127, No. 2, pp. 614-618 (2005) (published on Web Dec. 9, 2004).
Yuning Li et al., "Novel Peripherally Substituted Indolo[3,2-*b*]carbazoles for High-Mobility Organic Thin-Film Transistors," *Advanced Materials*, vol. 17, No. 7, pp. 849-853 (2005).

* cited by examiner

*Primary Examiner*—Taofiq A Solola
(74) *Attorney, Agent, or Firm*—Zosan Soong

(57) ABSTRACT

A compound composed of a plurality of optionally substituted indolocarbazole moieties which are the same or different from each other.

7 Claims, 2 Drawing Sheets

COMPOUND WITH INDOLOCARBAZOLE MOIETIES AND DEVICES CONTAINING SUCH COMPOUND

CROSS-REFERENCE TO RELATED APPLICATIONS

This application is a continuation-in-part application of co-pending U.S. application Ser. No. 11/011,678 (filing date Dec. 14, 2004) from which priority is claimed, the disclosure of which is totally incorporated herein by reference.

Yiliang Wu et al., U.S. application Ser. No. 11/167,485, filed on Jun. 27, 2005, titled "THIN FILM TRANSISTORS INCLUDING INDOLOCARBAZOLES" is a continuation-in-part application of co-pending U.S. application Ser. No. 11/011,441 (filing date Dec. 14, 2004) from which priority is claimed, the disclosure of which is totally incorporated herein by reference.

Yuning Li et al., U.S. application Ser. No. 11/011,901, filed on Dec. 14, 2004, titled "PROCESS TO FORM COMPOUND WITH INDOLOCARBAZOLE MOIETIES."

STATEMENT REGARDING FEDERALLY SPONSORED RESEARCH OR DEVELOPMENT

This invention was made with United States Government support under Cooperative Agreement No. 70NANBOH3033 awarded by the National Institute of Standards and Technology (NIST). The United States Government has certain rights in the invention.

BACKGROUND OF THE INVENTION

Organic electronics has been an intense research topic over the last two decades or so because of their enormous commercial potential. Some illustrative organic electronic devices are organic light-emitting diodes, organic thin film transistors, and organic photovoltaics. One of the key components in these devices is organic semiconductors which have received extensive research and development efforts. In the field of organic electronics, organic thin-film transistors (OTFTs) have in recent years attracted great attention as a low-cost alternative to mainstream amorphous silicon-based transistors for electronic applications. OTFTs are particularly suited for applications where large-area circuits (e.g., backplane electronics for large displays), desirable form factors and structural features (e.g., flexibility for e-paper), and affordability (e.g., ultra low cost for ubiquitous radio frequency identification tags) are essential.

Organic semiconductors are typically based on: (1) acenes such as tetracene, pentacene and their derivatives, (2) thiophenes such as oligothiophenes and polythiophenes, (3) fused-ring thiophene-aromatics and thiophene-vinylene/arylene derivatives. Most of these semiconductors are either insoluble in common organic solvents or sensitive to air, and are therefore not suitable for fabricating low-cost OTFTs via liquid patterning and deposition processes under ambient conditions. There is therefore a critical need addressed by embodiments of the present invention to develop liquid-processable and air stable organic semiconductor compounds to enable low-cost OTFTs. The present invention in embodiments also provides a facile process for the preparation of these organic semiconductors which meet the fabrication requirements for low-cost OTFTs.

The following documents provide background information:

Christos D. Dimitrakopoulos et al., "Organic Thin Film Transistors for Large Area Electronics," *Adv. Mater.*, Vol. 14, No. 2, pp. 99-117 (2002).

Salem Wakim et al., "Organic Microelectronics: Design, Synthesis, and Characterization of 6,12-Dimethylindolo[3,2-b]Carbazoles," *Chem. Mater.* Vol. 16, No. 23, pp. 4386-4388 (published on web Jul. 7, 2004).

Nan-Xing Hu et al., "5-11-Dihydro-5,11-di-1-naphthylindolo[3,2-b]carbazole: Atropisomerism in a Novel Hole-Transport Molecule for Organic Light-Emitting Diodes," *J. Am. Chem. Soc.*, Vol. 121, pp. 5097-5098 (1999).

Hu et al., U.S. Pat. No. 5,942,340.

Hu et al., U.S. Pat. No. 5,952,115.

Hu et al., U.S. Pat. No. 5,843,607.

SUMMARY OF THE DISCLOSURE

The present invention is accomplished in embodiments by providing a compound comprising a plurality of optionally substituted indolocarbazole moieties which are the same or different from each other.

In other embodiments, there is provided a compound comprising a plurality of optionally substituted indolocarbazole moieties, which are the same or different from each other, wherein the indolocarbazole moieties are independently selected from the structures (A), (B), (C), (D), (E), (F) and (G), or a mixture thereof:

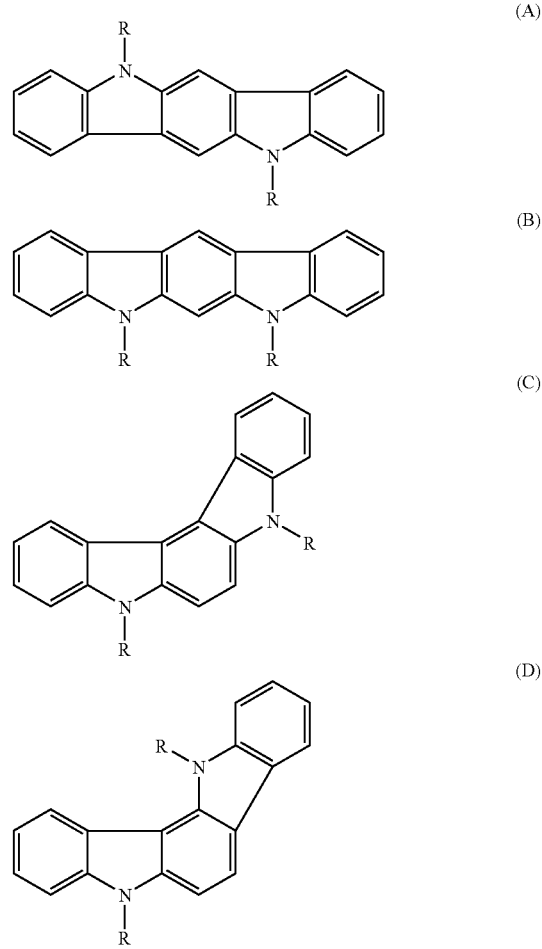

-continued

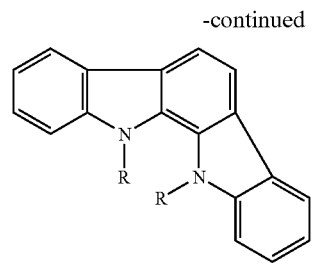
(E)

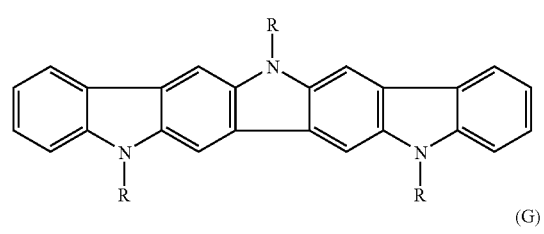
(F)

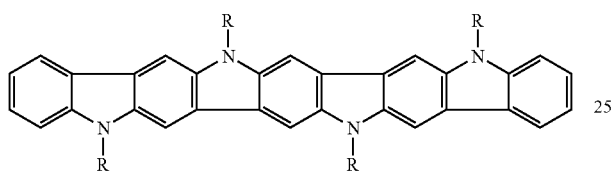
(G)

wherein for each of the structures (A) through (G), each R is independently selected from a group consisting of a hydrogen, a hydrocarbon group and a heteroatom-containing group, wherein each of the structures (A) through (G) is optionally peripherally substituted.

There is further provided in embodiments an electronic device comprising:

a substrate;

an electrically conductive layer or a dielectric layer, or both the electrically conductive layer and the dielectric layer; and a semiconductor layer comprising a compound comprising a plurality of optionally substituted indolocarbazole moieties which are the same or different from each other.

There is also provided in embodiments a thin film transistor comprising:

(a) a gate dielectric layer;
(b) a gate electrode;
(c) a semiconductor layer;
(d) a source electrode; and
(e) a drain electrode, wherein the gate dielectric layer, the gate electrode, the semiconductor layer, the source electrode, and the drain electrode are in any sequence as long as the gate electrode and the semiconductor layer both contact the gate dielectric layer, and the source electrode and the drain electrode both contact the semiconductor layer, and wherein the semiconductor layer includes a compound comprising a plurality of optionally substituted indolocarbazole moieties, which are the same or different from each other, wherein the indolocarbazole moieties are independently selected from the structures (A), (B), (C), (D), (E), (F) and (G), or a mixture thereof:

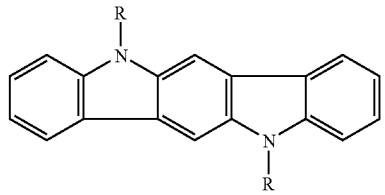
(A)

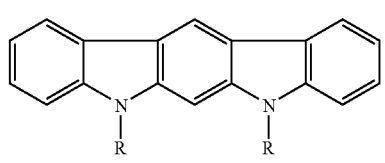
(B)

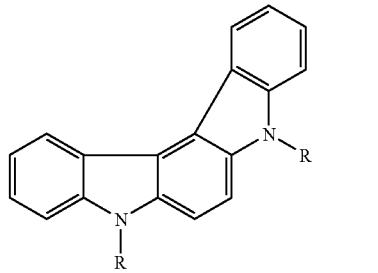
(C)

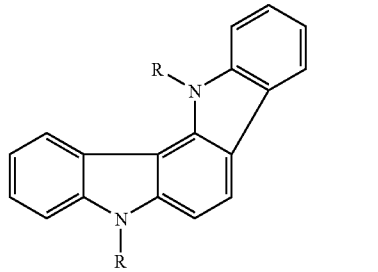
(D)

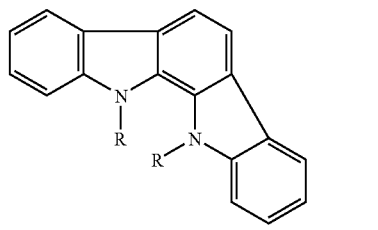
(E)

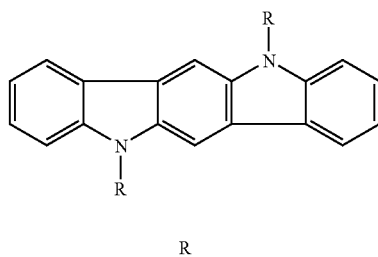
(F)

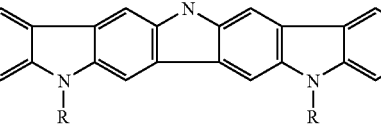
(G)

wherein for each of the structures (A) through (G), each R is independently selected from a group consisting of a hydrogen, a hydrocarbon group and a heteroatom-containing group, wherein each of the structures (A) through (G) is optionally peripherally substituted.

In additional embodiments, there is provided a process comprising:

reacting a reaction mixture comprised of one or more optionally substituted indolocarbazoles, a reaction medium, and a coupling agent at a reaction temperature to form a compound comprising a plurality of optionally substituted indolocarbazole moieties which are the same or different from each other.

In further embodiments, there is provided a process comprising:

reacting a reaction mixture comprised of one or more optionally substituted indolocarbazoles, a reaction medium, and a coupling agent at a reaction temperature to form a compound comprising a plurality of optionally substituted indolocarbazole moieties which are the same or different from each other, wherein the one or more optionally substituted indolocarbazoles are independently selected from the group consisting of structures (A), (B), (C), (D) (E), (F) and (G), or a mixture thereof:

(A)
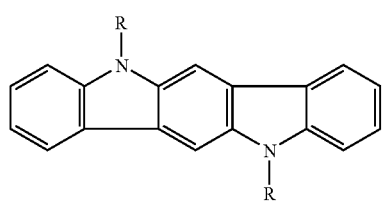

(B)
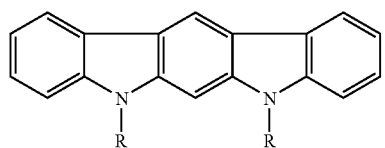

(C)
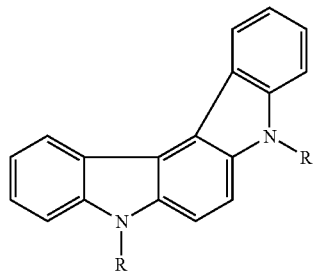

(D)
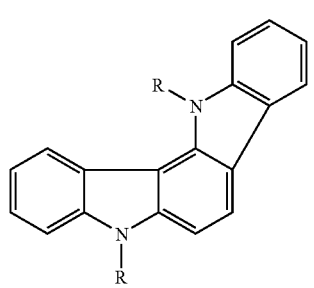

(E)
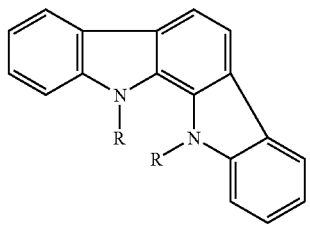

(F)
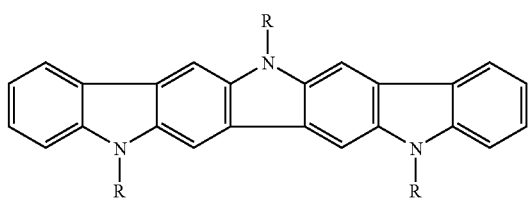

(G)
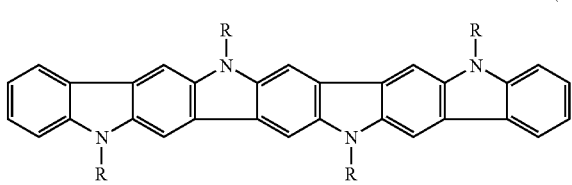

wherein for each of the structures (A) through (G), each R is independently selected from a group consisting of a hydrogen, a hydrocarbon group and a heteroatom-containing group, wherein each of the structures (A) through (G) is optionally peripherally substituted.

BRIEF DESCRIPTION OF THE DRAWINGS

Other aspects of the present invention will become apparent as the following description proceeds and upon reference to the following figures which represent exemplary embodiments.

Unless otherwise noted, the same reference numeral in different Figures refers to the same or similar feature.

DETAILED DESCRIPTION

Figure 1:
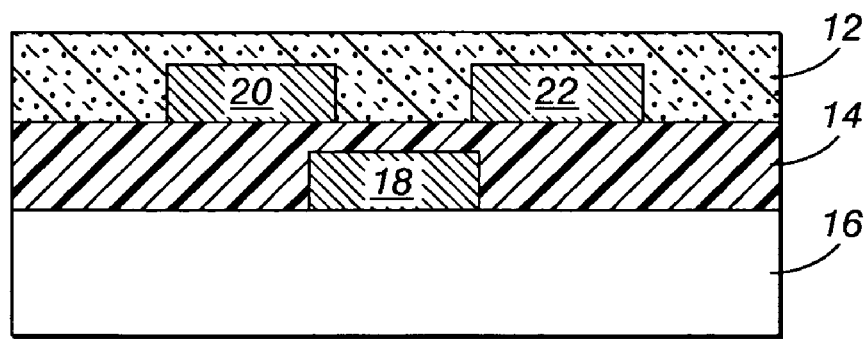
FIG. 1 represents a first embodiment of the present invention in the form of an OTFT.

The present compound ("Compound") is composed of a plurality of optionally substituted indolocarbazole moieties which are the same or different from each other wherein the Compound is synthesized from one or more optionally substituted indolocarbazoles. The terms "indolocarbazole moieties" and "indolocarbazole" refer to a structure composed of one carbazole moiety (optionally substituted) and one, two or more indolo moieties (each optionally substituted), wherein the carbazole moiety is fused with one or more of the indolo moieties, and any adjacent indolo moieties are fused together. The fusing of the carbazole moiety with the one or more indolo moieties, and the fusing of any adjacent indolo moieties can occur at any available positions. The carbazole moiety may be positioned at any suitable position in the structure such as at the end or the middle of the structure.

In embodiments, the Compound is a polymer, an oligomer, or a molecular compound. The polymer has a weight average molecular weight ($M_w$) of for example from about 5000 to about 1,000,000, and number average molecular weight ($M_N$) of for example from about 4000 to about 200,000 relative polystyrene standards as measured by gel permeation chromatography. The polymer could be a homopolymer, copolymer, or terpolymer, and the like. The oligomer refers to a mixture of low molecular weight Compounds which comprises a small number of repeating units of one or more chemical entities, and is therefore a subset of a polymer. The oligomer has a $M_w$ of for example less than 5000, and a $M_N$ of for example less than 4000. The molecular compound has a well-defined chemical structure with an exact molecular weight. It is understood that trace amounts of impurity may be present in the molecular compound. The molecular compound has a purity of, for example at least about 90% by weight, at least about 95% by weight, or at least about 99% by weight.

The Compound (a single Compound or a mixture of two or more different Compounds) may be used for any suitable applications, particularly as a semiconductor for electronic devices. The phrase "electronic devices" refers to macro-, micro- and/or nano-electronic devices such as thin film transistors, organic light emitting diodes, RFID tags, photovoltaic, and other electronic devices.

In embodiments, the Compound is unsubstituted or substituted with one or more substituents in any suitable substitution pattern. For substituted embodiments of the Compound, the substitution can be for example the following: (1) one or more nitrogen substitutions with no peripheral substitution; (2) one or more peripheral substitutions with no nitrogen substitution; or (3) one or more nitrogen substitutions and one or more peripheral substitutions. In embodiments, all the nitrogen atoms of the Compound are substituted with the same or different substituents, with the Compound being optionally peripherally substituted. In embodiments, the Compound is nitrogen substituted (and optionally peripherally substituted) wherein the one or more nitrogen substituents are independently selected from the group consisting of a hydrocarbon group and a heteroatom-containing group, or a mixture thereof. In embodiments, the Compound is peripherally substituted (and optionally nitrogen substituted) wherein the one or more peripheral substituents are independently selected from the group consisting of a hydrocarbon group, a heteroatom-containing group, and a halogen, or a mixture thereof.

The phrases "peripherally substituted" and "peripheral substitution" refer to at least one substitution (by the same or different substituents) on any one or more aromatic rings of the Compound regardless whether the aromatic ring is a terminal aromatic ring or an internal aromatic ring (that is, other than at a terminal position).

In embodiments, the indolocarbazole moieties of the Compound are independently selected from the group consisting of structures (A), (B), (C), (D), (E), (F), and (G), or a mixture thereof.

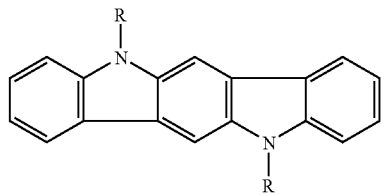
(A)

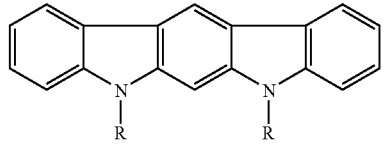
(B)

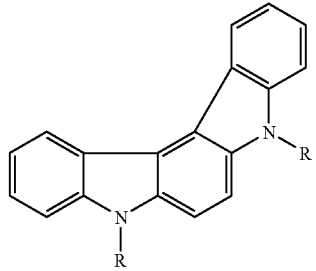
(C)

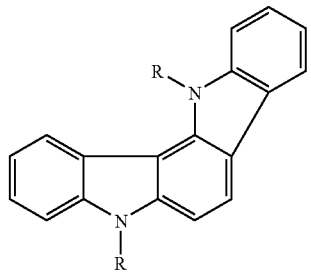
(D)

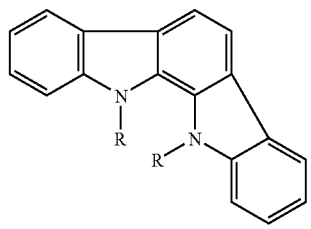
(E)

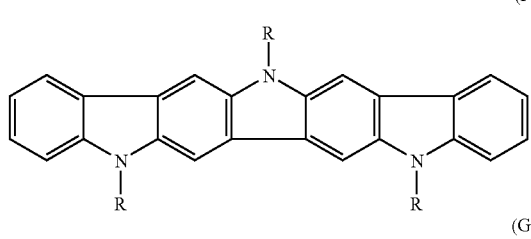
(F)

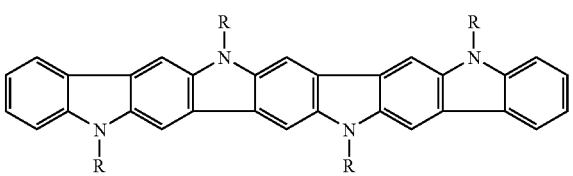
(G)

wherein for each of the structures (A) through (G), each R is independently selected from a group consisting of a hydrogen, a hydrocarbon group and a heteroatom-containing group (that is, each nitrogen atom can have the same or different R), wherein each of the structures (A) through (G) is optionally peripherally substituted by one or more substituents selected from the group consisting of a hydrocarbon group, a heteroatom-containing group, and a halogen, or a mixture thereof.

It is noted that structures (A) through (G) are discussed in two contexts. In the context of the optionally substituted indolocarbazole moieties, structures (A) through (G) are moieties depicted without the covalent bonding which connects adjacent indolocarbazole moieties but it is understood that in the Compound adjacent indolocarbazole moieties of structures (A) through (G) are covalent bonded. In the context of optionally substituted indolocarbazoles useful in the synthesis of the Compound, structures (A) through (G) are exemplary indolocarbazoles.

The optionally substituted indolocarbazoles moieties are covalent bonded at any suitable position to form the Compound. As an illustration for structure (A), the covalent bonding can occur at 2 and 8 positions or 3 and 9 positions depending on reactions and reaction conditions. For example, using indolocarbazole of structure (A) as the starting materials, treatment with $FeCl_3$ can lead to covalent bonding at the 2 and 8 positions of structure (A). On the other hand, if 3,9-dibromoindolocarbazole is used as the starting material and treated with Zn in the presence of $NiCl_2/2,2'$-dipyridil, then covalent bonding will occur at the 3 and 9 positions of structure (A).

The hydrocarbon group for the optionally substituted indolocarbazole moieties contains for example from 1 to about 50 carbon atoms, or from 1 to about 30 carbon atoms, and may be for example a straight chain alkyl group, a branched alkyl group, a cyclic aliphatic group, an aryl group, an alkylaryl group, and an arylalkyl group. Exemplary hydrocarbon groups include for example methyl, ethyl, propyl, butyl, pentyl, hexyl, heptyl, octyl, nonyl, decyl, undecyl, dodecyl, tridecyl, tetradecyl, pentadecyl, cyclopentyl, cyclohexyl, cycloheptyl, and isomers thereof.

The heteroatom-containing group for the optionally substituted indolocarbazole moieties has for example 2 to about 200 atoms, or from 2 to about 100 atoms) and may be for example a nitrogen-containing group, an alkoxy group, a heterocyclic system, an alkoxyaryl, an arylalkoxy, and a halogenated hydrocarbon (where the halogen is for example fluorine, bromine, chlorine, or iodine, or a mixture thereof). Exemplary heteroatom-containing groups include for example fluoroalkyl, fluoroaryl, cyano, nitro, carbonyl, carboxylate, amino (optionally substituted with one or two substituents such as for example a hydrocarbon group described herein), and alkoxy (having for example 1 to about 18 carbon atoms). In embodiments, the heteroatom-containing group is independently selected from the group consisting of fluoroalkyl (having for example 1 to about 18 carbon atoms), fluoroaryl, cyano, nitro, carbonyl, carboxylate, alkoxy (having for example 1 to about 18 carbon atoms), and amino (optionally substituted with one or two substituents such as for example a hydrocarbon group described herein), or a mixture thereof. In embodiments, the heteroatom-containing group is an optionally substituted carbazole group.

In embodiments, the heteroatom-containing group is an optionally substituted thienyl comprising one, two, or more thienyl units, each thienyl unit being the same or different from each other and of exemplary structure (A)

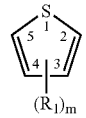

(A)

where $R_1$ is independently selected from a hydrocarbon group (such as those described herein for the optionally substituted indolocarbazole moieties), a heteroatom containing group (such as those described herein for the optionally substituted indolocarbazole moieties), and a halogen (such as those described herein for the optionally substituted indolocarbazole moieties), and where m is 0, 1, 2 or 3.

In embodiments, $R_1$ is part of a cyclic ring structure fused to the thienyl unit, where the fused cyclic ring structure is of any size such as for example a 4 to 8 membered ring, particularly, a 5 or 6 membered ring, wherein $R_1$ is attached at the carbon atoms at for example the third ring position and the fourth ring position of the thienyl unit, or any other available ring positions. The fused ring structure (containing $R_1$) may be either a hydrocarbon group described herein or a heteroatom containing group described herein. Where $R_1$ is part of a ring structure fused to a thienyl unit, m is 1 even though $R_1$ in this situation is bonded to two positions of the thienyl unit. Examples of the thienyl unit with $R_1$ being part of a ring substituent structure are the following:

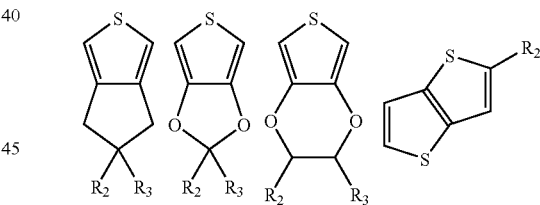

wherein $R_2$ and $R_3$ are the same or different from each other, and are selected from the group consisting of:
(a) a hydrocarbon group (such as those described herein for the optionally substituted indolocarbazole moieties),
(b) a heteroatom containing group (such as those described herein for the optionally substituted indolocarbazole moieties),
(c) a halogen (such as those described herein for the optionally substituted indolocarbazole moieties), and
(d) a hydrogen.

The halogen for the optionally substituted indolocarbazole moieties is fluorine, bromine, chlorine, or iodine, or a mixture thereof.

The number of optionally substituted indolocarbazole moieties in the Compound is for example 2 to about 500, or 2 to about 100.

Illustrative Compounds are structures (1) through (6):
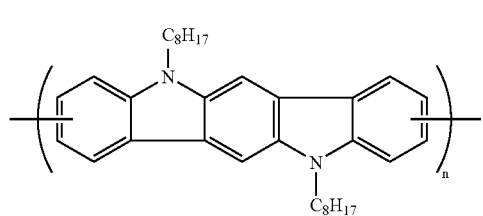
(1)
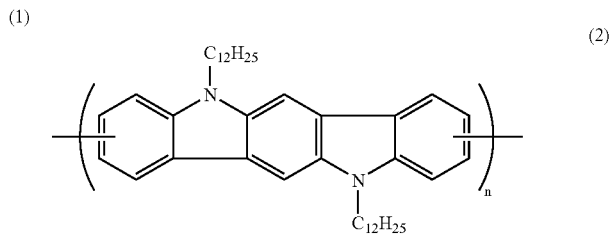
(2)
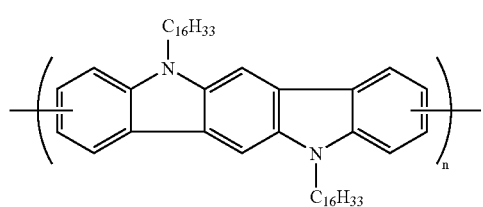
(3)
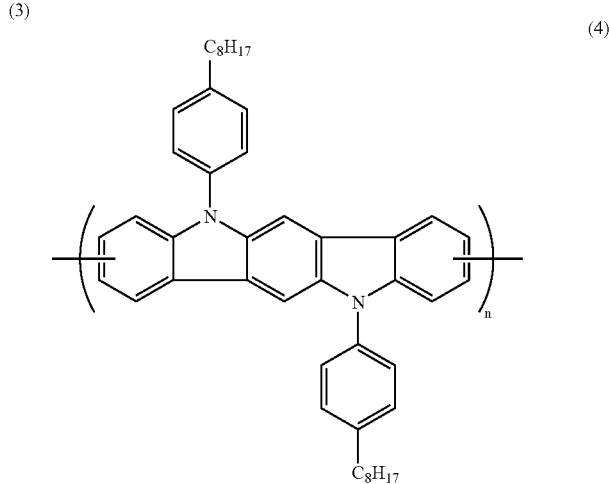
(4)
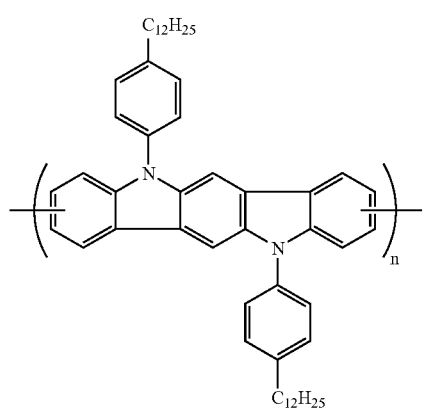
(5)
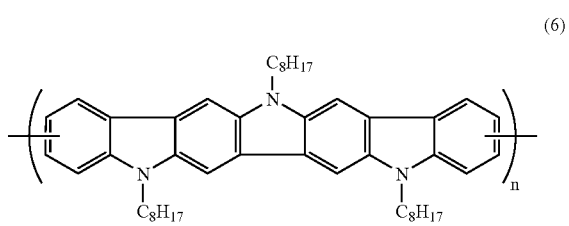
(6)
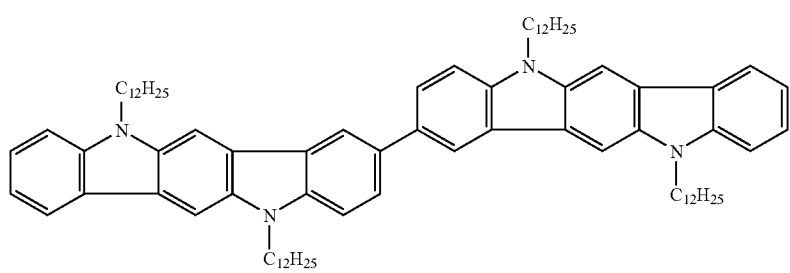
(7)

(8)

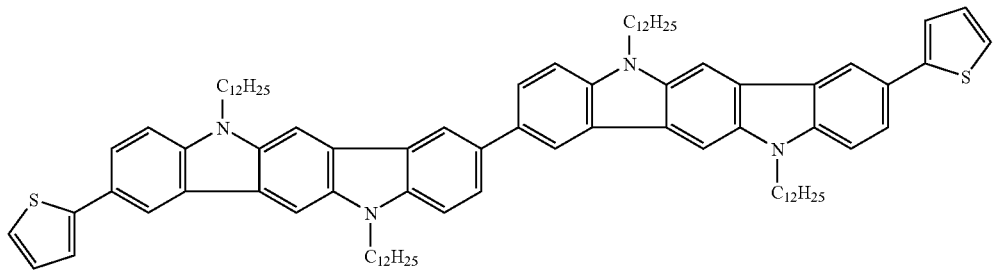

(9)

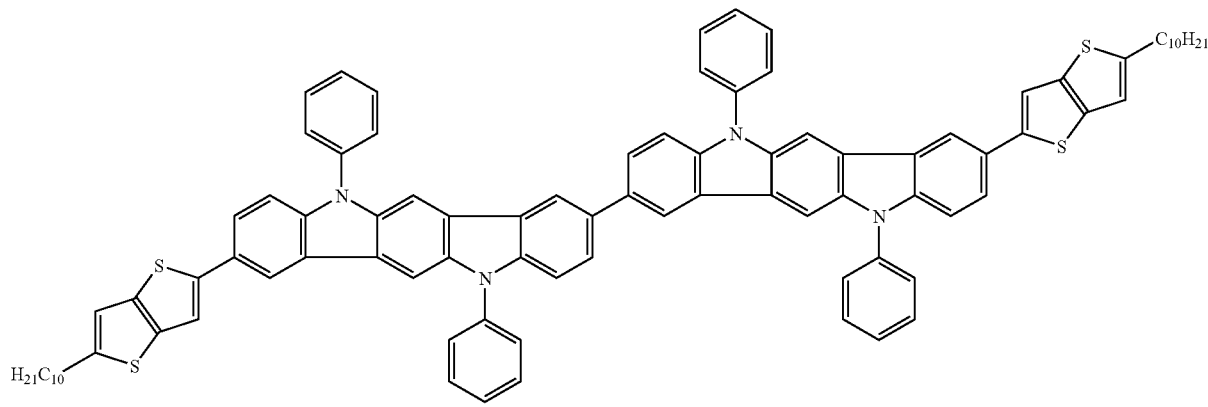

(10)

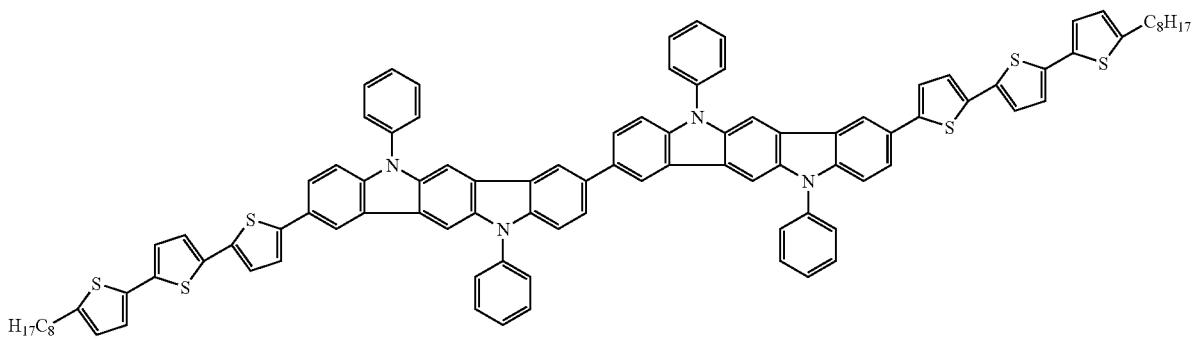

where n is an integer such as for example 2 to about 500, or 2 to about 100.

Other exemplary embodiments of the Compound include for example poly(5,7-dialkylindolo[2,3-b]carbazole)s, poly(5,7-diarylindolo[2,3-b]carbazole)s, poly(5,8-dialkylindolo[2,3-c]carbazole)s, poly(5,8-diaryl indolo[2,3-c]carbazole)s, poly(5,10-dialkylindolo[3,2-a]carbazole)s, poly(5,10-diarylindolo[3,2-a]carbazole)s, poly(5,12-dialkylindolo[3,2-c]carbazole)s, poly(5,12-diarylindolo[3,2-c]carbazole)s, poly(1,12-dialkylindolo[2,3-a]carbazole)s, and poly(11,12-diarylindolo[2,3-a]carbazole)s.

In embodiments, a composition may be prepared which comprises two or more Compounds in any suitable ratio by weight such as for example a ratio ranging from about 1% (first Compound):99% (second Compound) to about 99% (first Compound):1% (second Compound).

To be an efficient semiconductor for OTFTs, the optionally substituted Compound in embodiments provides (i) proper molecular ordering conducive to charge carrier transport; and (ii) sufficient stabilization to charge carriers to enable efficient charge carrier injection. In embodiments, the Compound has one or more strategically placed substituents comprising for example at least one long chain alkyl group (having for example about 6 to about 18 carbon atoms in length) to promote molecular self-assembly, thus forming proper molecular ordering for charge carrier transport. In embodiments, the Compound also has one or more strategically placed substituents such as for example aryl substituents at the nitrogen positions to provide stabilization to injected charge carriers. In embodiments, to provide stabilization to injected charge carriers, the Compound is substituted with one or more substituents independently selected from the group consisting of a long chain alkyl group (having for example about 6 to about 18 carbon atoms in length), an alkylphenyl (the alkyl of the alkylphenyl having for example 1 to about 18 carbon atoms in length), a phenyl, a chloro, an alkoxy (having for example 1 to about 18 carbon atoms), and an amino (optionally substituted with one or two substituents such as for example a hydrocarbon group described herein), or a mixture thereof.

The Compound may be a p-type semiconductor or n-type semiconductor, depending very much on the nature of the substituents. Substituents which possess an electron donating property such as alkyl, alkoxy and aryl groups, when present in the Compound, render the Compound a p-type semiconductor. On the other hand, substituents which are electron withdrawing such as cyano, nitro, fluorinated alkyl, and fluorinated aryl groups may transform the Compound into the n-type semiconductor.

In embodiments, the optionally substituted Compound has a band gap of for example greater than about 1.8 eV, greater than about 2.0 eV, or greater than about 2.5 eV. The corresponding highest occupied molecular orbital (HOMO) energy level of the optionally substituted Compound is for example lower than about 4.9 eV from vacuum, preferably lower than about 5.1 eV from vacuum. The optionally substituted Compound are in embodiments relatively stable against oxygen doping in air by virtue of their relatively low lying HOMOs.

In embodiments, the relatively low-lying HOMOs and large band gaps of the optionally substituted Compound generally provides many advantages over other semiconductors. For example, in embodiments, the optionally substituted Compound generally has no or little absorbance in the visible region of the spectrum, and is therefore expected to be photochemically stable when exposed to light.

The Compound can be prepared by an appropriate coupling reaction of an optionally substituted indolocarbazole (a single optionally substituted indolocarbazole or a mixture of two or more different optionally substituted indolocarbazoles in any suitable ratios). The coupling agent or coupling agents may be for example an oxidizing agent. An illustrative preparation of the Compound using an oxidative coupling reaction involves reacting a reaction mixture comprising a solvent (a single solvent or a mixture of two or more different solvents in any suitable ratios), an oxidizing agent (a single oxidizing agent or a mixture of two or more different oxidizing agents in any suitable ratio), and an optionally substituted indolocarbazole (a single optionally substituted indolocarbazole or a mixture of two or more different optionally substituted indolocarbazoles in any suitable ratios) at a suitable reaction temperature. By controlling the ratio of coupling agent to optionally substituted indolocarbazole under various reaction conditions (e.g., reaction temperature, length of reaction time, etc.), dimeric, oligomeric, or polymeric Compound can be selectively synthesized. In embodiments, the Compound can be further substituted after the appropriate coupling reaction. For example, the illustrative Compound (8) can be obtained by further substituting the illustrative Compound (7) with two thienyl groups.

Any suitable optionally substituted indolocarbazole may be used to form the Compound such as for example the optionally substituted indolocarbazole selected from the group consisting of structures (A) through (G), or a mixture thereof and from the group consisting of the structures (I) through (VIII), or a mixture thereof. The optionally substituted indolocarbazoles can be made with any suitable synthetic methods. The optionally substituted indolocarbazoles and the synthesis methods are disclosed for example in U.S. Pat. Nos. 5,942,340; 5,952,115; and 5,843,607, which are totally incorporated herein by reference.

Illustrative optionally substituted indolocarbazoles used to make the Compound are for example structures (I) through (VIII):

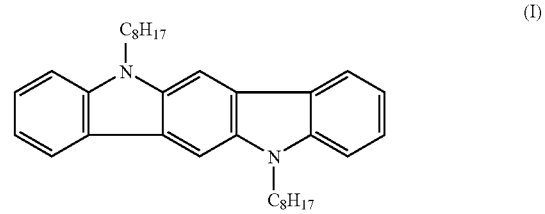
(I)

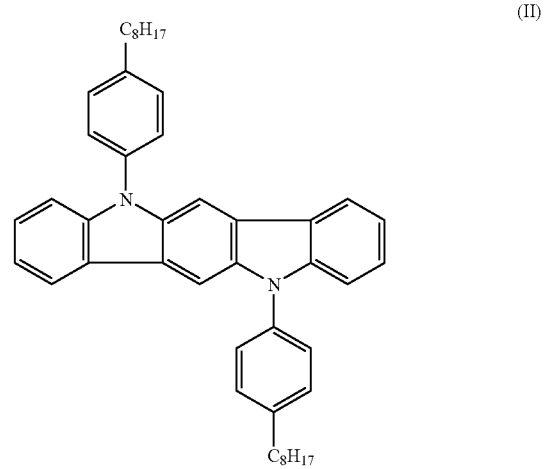
(II)

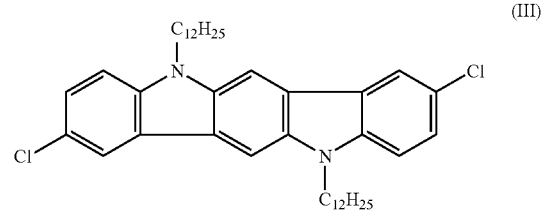
(III)

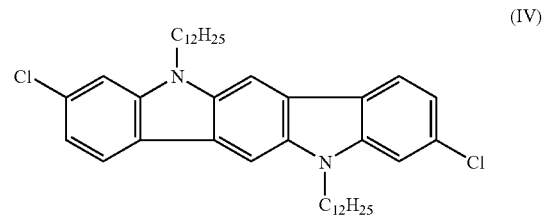
(IV)

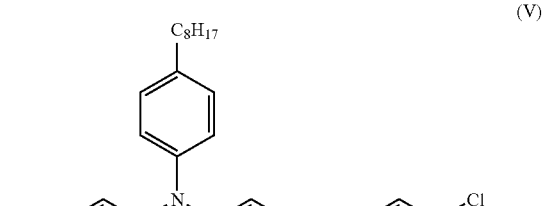

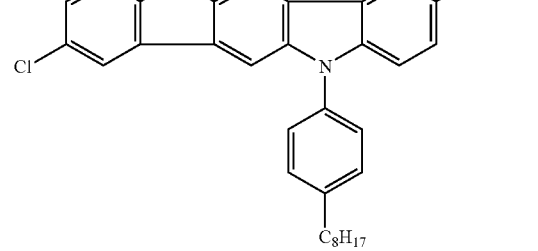
(V)

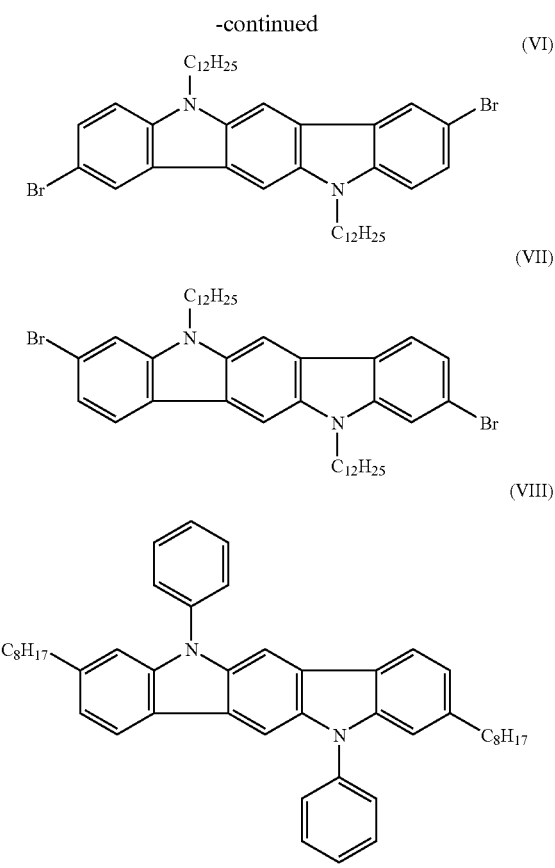

The reaction medium may be for example water or an organic reaction medium such as for example chloroform, dichloromethane, chlorobenzene, dichlorobenzene, and the like, and mixtures thereof at any suitable ratio. In embodiments, the reaction medium is a solvent for one or more components of the reaction mixture.

Any suitable coupling agent may be used. Illustrative coupling agents, particularly oxidizing agents, are for example $FeCl_3$, $FeBr_3$, $Fe_2(SO_4)_3$, $RuCl_3$, $MoCl_5$, $Na_2S_2O_8$, $K_2S_2O_8$, $K_2Cr_2O_7$, $KMnO_4$, $KBrO_3$, $KClO_3$, and the link, and mixtures thereof. The molar ratio of coupling agent to optionally substituted indolocarbazole is for example from 1 to 20, or from 2 to 10. The reaction temperature may be for example from about −40° C. to about 200° C., or from about −20° C. to about 150° C., or from about 0° C. to about 100° C. The length of the reaction time can range for example from about 1 hour to about 72 hours.

The desired Compound can be isolated for example by adding the reaction mixture to a non-solvent or a poor solvent of the Compound. A non-solvent refers to any liquid in which the Compound is insoluble. A poor solvent refers to any liquid in which the Compound has low solubility. Suitable non-solvents or poor solvents of the Compound may include for example methanol, ethanol, propanol, acetone, and the like, and mixtures thereof. After isolation by precipitation from a non-solvent or a poor solvent, the Compound may be optionally treated with aqueous ammonia solution, a hydrazine solution, triethylamine, or other suitable base. The Compound can then be further purified by repeated precipitation, extraction with one or more solvents, column chromatography, sublimation, or other conventional techniques to remove residual coupling agent and other undesired by-products.

The Compound can be optionally further purified by extraction via for example Soxhlet extraction using one or more non-solvents or poor solvents of the Compound to remove trace impurities and/or, in the case of a polymeric compound, low molecular weight fractions.

Any suitable techniques may be used to form the semiconductor layer containing the Compound. One such method is by vacuum evaporation at a vacuum pressure of about $10^{-5}$ to $10^{-7}$ torr in a chamber containing a substrate and a source vessel that holds the Compound in powdered form. Heat the vessel until the Compound sublimes onto the substrate. The performance of the films containing the Compound may depend on the rate of heating, the maximum source temperature and substrate temperature during the evaporation process. In embodiments, solution deposition techniques may also be used to fabricate the semiconductor layer comprised of the Compound. Solution deposition techniques refer to liquid deposition processes such as spin coating, blade coating, rod coating, screen printing, ink jet printing, stamping and the like. Specifically, the Compound can be dissolved in a suitable solvent of for example tetrahydrofuran, dichloromethane, chlorobenzene, toluene, and xylene to form a solution at a concentration of about 0.1% to about 10%, particularly about 0.5% to about 5% by weight, and then used in solution deposition. Illustrative deposition by spin coating can be carried out at a spin speed of about 500 to about 3000 rpm, particularly about 1000 to about 2000 rpm for a period of time of about 5 to about 100 seconds, particularly about 30 to about 60 seconds at room temperature or an elevated temperature to form a thin film on a suitable substrate such as silicon wafer, glass, or plastic film.

The semiconductor layer may be predominantly amorphous or predominantly crystalline in nature, depending on the Compound and processing conditions. The semiconductor layer can be characterized by common characterization techniques such as X-ray diffraction, atomic force microscopy, optical microscopy, etc. For example, a predominantly amorphous layer usually shows broad X-ray diffraction peaks, while a predominantly crystalline layer generally exhibits sharp X-ray diffraction peaks. The degree of crystallinity of a semiconductor layer can be calculated from the integrated area of diffraction peaks. In embodiments, the phrase "predominately crystalline" indicates that the crystallinity of the semiconductor layer is for example larger than about 50%, larger than about 80%, or larger than about 90%.

Depending on the nature of the Compound, a predominantly crystalline semiconductor layer can be formed by a number of techniques. For example, a predominantly crystalline semiconductor layer can be formed by vacuum evaporation of the Compound onto a substrate holding at an elevated temperature of for example about 50° C. to about 120° C. In another technique, a predominantly crystalline semiconductor layer can be achieved by solution coating followed by controlled solvent evaporation and optionally post-deposition annealing at an elevated temperature of for example about 80° C. to about 250° C.

The exemplary use of Compound as a semiconductor in electronic devices is illustrated herein using thin film transistors.

In FIG. 1, there is schematically illustrated an OTFT configuration 10 comprised of a substrate 16, in contact therewith a metal contact 18 (gate electrode) and a layer of a gate dielectric layer 14 on top of which two metal contacts, source electrode 20 and drain electrode 22, are deposited. Over and between the metal contacts 20 and 22 is an organic semiconductor layer 12 as illustrated herein.

Figure 2:
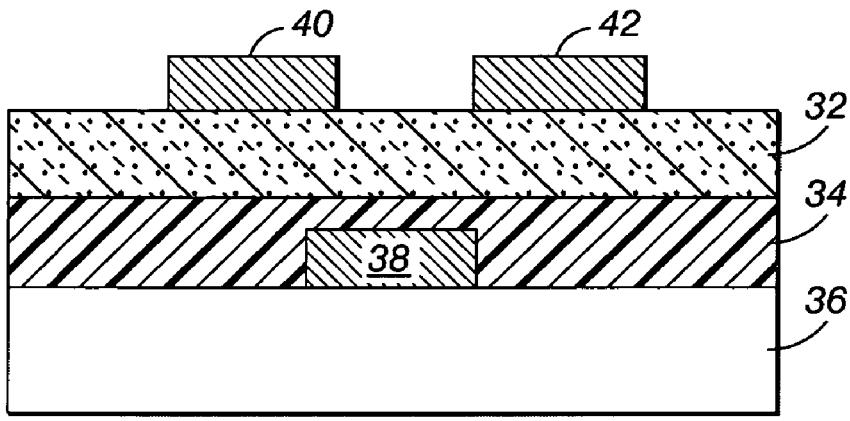
FIG. 2 represents a second embodiment of the present invention in the form of an OTFT.

FIG. 2 schematically illustrates another OTFT configuration 30 comprised of a substrate 36, a gate electrode 38, a source electrode 40 and a drain electrode 42, a gate dielectric layer 34, and an organic semiconductor layer 32.

Figure 3:
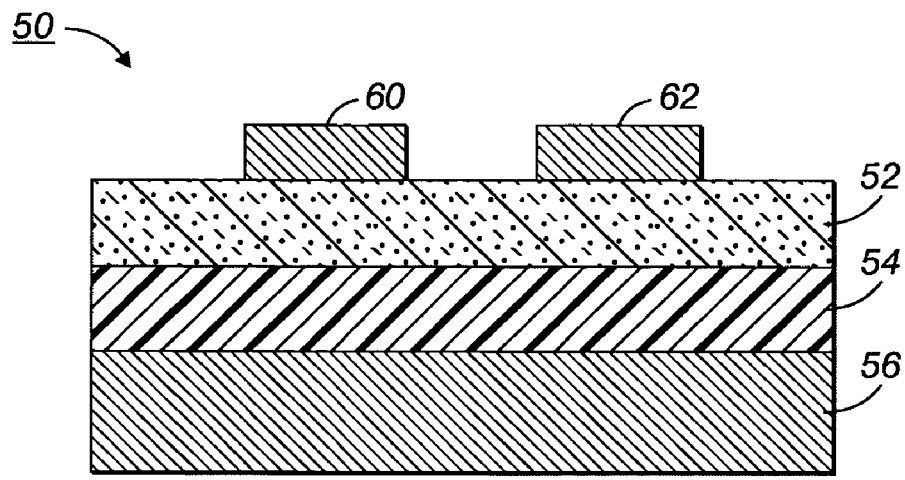
FIG. 3 represents a third embodiment of the present invention in the form of an OTFT.

FIG. 3 schematically illustrates a further OTFT configuration 50 comprised of a heavily n-doped silicon wafer 56 which acts as both a substrate and a gate electrode, a thermally grown silicon oxide gate dielectric layer 54, and an organic semiconductor layer 52, on top of which are deposited a source electrode 60 and a drain electrode 62.

Figure 4:
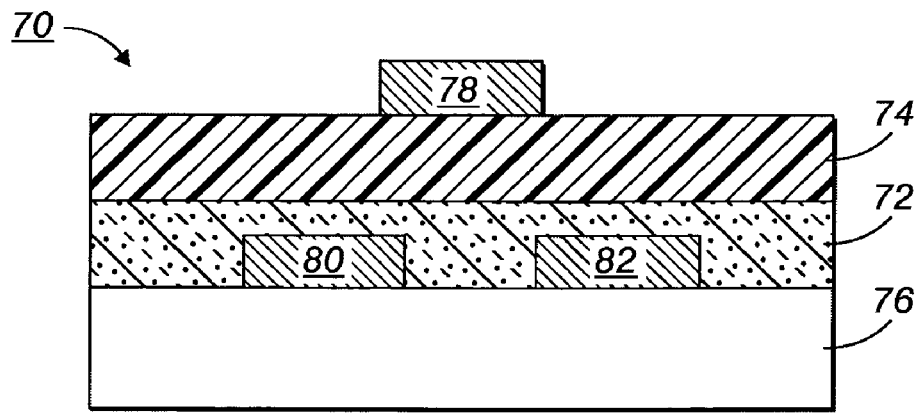
FIG. 4 represents a fourth embodiment of the present invention in the form of an OTFT.

FIG. 4 schematically illustrates an additional OTFT configuration 70 comprised of substrate 76, a gate electrode 78, a source electrode 80, a drain electrode 82, an organic semiconductor layer 72, and a gate dielectric layer 74.

The composition and formation of the semiconductor layer are described herein.

The semiconductor layer has a thickness ranging for example from about 10 nanometers to about 1 micrometer with a preferred thickness of from about 20 to about 200 nanometers. The OTFT devices contain a semiconductor channel with a width W and length L. The semiconductor channel width may be, for example, from about 1 micrometers to about 5 millimeters, with a specific channel width being about 5 micrometers to about 1 millimeter. The semiconductor channel length may be, for example, from about 1 micrometer to about 1 millimeter with a more specific channel length being from about 5 micrometers to about 100 micrometers.

The substrate may be composed of for instance silicon, glass plate, plastic film or sheet. For structurally flexible devices, a plastic substrate, such as for example polyester, polycarbonate, polyimide sheets and the like may be preferred. The thickness of the substrate may be from about 10 micrometers to over about 10 millimeters with an exemplary thickness being from about 50 to about 100 micrometers, especially for a flexible plastic substrate and from about 1 to about 10 millimeters for a rigid substrate such as glass plate or silicon wafer.

The gate electrode can be a thin metal film, a conducting polymer film, a conducting film made from conducting ink or paste, or the substrate itself can be the gate electrode, for example heavily doped silicon. Examples of gate electrode materials include but are not restricted to aluminum, gold, chromium, indium tin oxide, conducting polymers such as polystyrene sulfonate-doped poly(3,4-ethylenedioxythiophene) (PSS-PEDOT), conducting ink/paste comprised of carbon black/graphite or colloidal silver dispersion in polymer binders, such as ELECTRODAG™ available from Acheson Colloids Company. The gate electrode layer can be prepared by vacuum evaporation, sputtering of metals or conductive metal oxides, coating from conducting polymer solutions or conducting inks by spin coating, casting or printing. The thickness of the gate electrode layer ranges for example from about 10 to about 200 nanometers for metal films and in the range of about 1 to about 10 micrometers for polymer conductors.

The source and drain electrode layers can be fabricated from materials which provide a low resistance ohmic contact to the semiconductor layer. Typical materials suitable for use as source and drain electrodes include those of the gate electrode materials such as gold, nickel, aluminum, platinum, conducting polymers and conducting inks. Typical thicknesses of source and drain electrodes are about, for example, from about 40 nanometers to about 10 micrometers with the more specific thickness being about 100 to about 400 nanometers.

The gate dielectric layer generally can be an inorganic material film or an organic polymer film. Illustrative examples of inorganic materials suitable as the gate dielectric layer include silicon oxide, silicon nitride, aluminum oxide, barium titanate, barium zirconium titanate and the like; illustrative examples of organic polymers for the gate dielectric layer include polyesters, polycarbonates, poly(vinyl phenol), polyimides, polystyrene, poly(methacrylate)s, poly(acrylate)s, epoxy resin and the like. The thickness of the gate dielectric layer is, for example from about 10 nanometers to about 500 nanometers depending on the dielectric constant of the dielectric material used. An exemplary thickness of the gate dielectric layer is from about 100 nanometers to about 500 nanometers. The gate dielectric layer may have a conductivity that is for example less than about $10^{-12}$ S/cm.

The gate dielectric layer, the gate electrode, the semiconductor layer, the source electrode, and the drain electrode are formed in any sequence with in embodiments the gate electrode and the semiconductor layer both contacting the gate dielectric layer, and the source electrode and the drain electrode both contacting the semiconductor layer. The phrase "in any sequence" includes sequential and simultaneous formation. For example, the source electrode and the drain electrode can be formed simultaneously or sequentially. The composition, fabrication, and operation of field effect transistors are described in Bao et al., U.S. Pat. No. 6,107,117, the disclosure of which is totally incorporated herein by reference.

For a p-channel OTFT, the source electrode is grounded and a bias voltage of generally, for example, about 0 volt to about −80 volts is applied to the drain electrode to collect the charge carriers transported across the semiconductor channel when a voltage of generally about +20 volts to about −80 volts is applied to the gate electrode.

The semiconductor layer comprising the Compound in an OTFT device generally exhibit a field-effect mobility of greater than for example about $10^{-3}$ cm$^2$/Vs (square centimeter per Volt per second), and an on/off ratio of greater than for example about $10^3$. On/off ratio refers to the ratio of the source-drain current when the transistor is on to the source-drain current when the transistor is off.

The invention will now be described in detail with respect to specific exemplary embodiments thereof, it being understood that these examples are intended to be illustrative only and the invention is not intended to be limited to the materials, conditions, or process parameters recited herein. All percentages and parts are by weight unless otherwise indicated. As used herein, room temperature refers to a temperature ranging for example from about 20 to about 25° C.

EXAMPLE 1

(a) Synthesis of
Poly(5,11-Dioctylindolo[3,2-b]Carbazole)

A solution of 5,11-dioctylindolo[3,2-b]carbazole (0.481 g, 1.0 mmol) in chlorobenzene (10 mL) was added dropwise to a stirring mixture of FeCl$_3$ (0.681 g, 4.2 mmol) and chlorobenzene (20 mL) in a 100 mL flask at 0° C. under an argon atmosphere. The solution became dark blue immediately upon addition. After stirring for 48 h at room temperature, the reaction mixture was poured into methanol (200 mL). The precipitated solid product was washed with water and methanol. After washing, the product was suspended in dichloromethane (100 mL) with stirring while aqueous ammonia solution (30%, 20 mL) was added. After stirring for 12 h, the mixture was added to methanol. The solid product was collected and subject to Soxhlet extraction, first with methanol for 24 h and then with heptane for another 24 h. The remaining solid product was isolated by Soxhlet extraction with refluxing chlorobenzene. The resulting chlorobenzene solution was concentrated and then added to 100 mL of stirring methanol to precipitate the product. The solid product was dried under a reduced pressure overnight. Yield: 0.38 g.

(b) OTFT Fabrication and Evaluation

A top-contact thin film transistor configuration as schematically illustrated, for example, in FIG. 3 was selected as our test device structure. The test device was built on an n-doped silicon wafer with a thermally grown silicon oxide layer with a thickness of about 110 nanometers thereon, and had a capacitance of about 30 nF/cm² (nanofarads/square centimeter), as measured with a capacitor meter. The wafer functioned as the gate electrode while the silicon oxide layer acted as the gate dielectric. The silicon wafer was first cleaned with isopropanol, argon plasma, isopropanol and air dried, and then immersed in a 0.1 M solution of octyltrichlorosilane (OTS-8) in toluene at 60° C. for 20 min. Subsequently, the wafer was washed with toluene, isopropanol and air-dried. A solution of poly(5,11-dioctylindolo[3,2-b]carbazole) dissolved in dichlorobenzene (0.3 percent by weight) was first filtered through a 1.0 micrometer syringe filter, and then spin-coated on the OTS-8-treated silicon wafer at 1000 rpm for 120 seconds at room temperature. This resulted in the formation of a semiconductor layer with a thickness of 20-50 nanometers on the silicon wafer, which was then dried in a vacuum oven at 80° C. for 5-10 h. Subsequently, gold source and drain electrodes of about 50 nanometers in thickness were deposited on top of the semiconductor layer by vacuum deposition through a shadow mask with various channel lengths and widths, thus creating a series of transistors of various dimensions.

The evaluation of transistor performance was accomplished in a black box (that is, a closed box which excluded ambient light) at ambient conditions using a Keithley 4200 SCS semiconductor characterization system. The carrier mobility, $\mu$, was calculated from the data in the saturated regime (gate voltage, $V_G$<source-drain voltage, $V_{SD}$) according to equation (1)

$$I_{SD} = C_i \mu (W/2L)(V_G - V_T)^2 \tag{1}$$

where $I_{SD}$ is the drain current at the saturated regime, W and L are, respectively, the semiconductor channel width and length, $C_i$ is the capacitance per unit area of the gate dielectric layer, and $V_G$ and $V_T$ are, respectively, the gate voltage and threshold voltage. $V_T$ of the device was determined from the relationship between the square root of $I_{SD}$ at the saturated regime and $V_G$ of the device by extrapolating the measured data to $I_{SD}=0$.

The transfer and output characteristics of the devices showed that the Compound was a p-type semiconductor. Using transistors with a dimension of W=5,000 µm and L=90 µm, the following average properties from at least five transistors were obtained:

Mobility: 2.1-2.8×10⁻³ cm²/Vs
On/off ratio: 10⁴~10⁵.

EXAMPLE 2

(a) Synthesis of Poly(5,11-Bis(4-Octylphenyl)Indolo[3,2-b]Carbazole)

A solution of 5,11-bis(4-octylphenyl)indolo[3,2-b]carbazole (0.50 g, 0.79 mmol) in chlorobenzene (10 mL) was added dropwise to a stirring mixture of FeCl₃ (0.58 g, 3.56 mmol) and chlorobenzene (10 mL) in a 100 mL flask at room temperature under an argon atmosphere. The resulting mixture was stirred at 50° C. for 48 h and then poured into a stirring methanol (200 mL). The precipitated solid product was washed with water and methanol, and then suspended in dichloromethane (100 mL) while aqueous ammonia solution (30%, 20 mL) was added. The resulting mixture was stirred for 12 h and then added to 100 mL of stirring methanol. The solid product was collected and subjected to Soxhlet extraction, first with methanol for 24 h and then with heptane for 24 h. The remaining insoluble solid product was isolated by Soxhlet extraction with refluxing chlorobenzene. The resulting chlorobenzene solution was concentrated and then added to a stirring methanol (100 mL) to precipitate the product. The solid product was dried under a reduced pressure overnight. Yield: 0.30 g.

(b) OTFT Device Fabrication and Evaluation

OTFT devices using poly(5,11-bis(4-octylphenyl)indolo[3,2-b]carbazole) as the semiconductor were fabricated and characterized in accordance with the procedures of Example 1. Using transistors with a dimension of W=5,000 µm and L=90 µm, the following average properties from at least five transistors were obtained:

Mobility: 1.3-1.8×10⁻³ cm²/Vs
On/off ratio: 10⁴~10⁵.

The mobility and current on/off ratio achieved by embodiments of the present thin film transistor devices are useful for various applications in electronics such as for example electronic paper.

The invention claimed is:
1. A thin film transistor comprising:
 (a) a gate dielectric layer;
 (b) a gate electrode;
 (c) a semiconductor layer;
 (d) a source electrode; and
 (e) a drain electrode,
wherein the gate dielectric layer, the gate electrode, the semiconductor layer, the source electrode, and the drain electrode are in any sequence as long as the gate electrode and the semiconductor layer both contact the gate dielectric layer, and the source electrode and the drain electrode both contact the semiconductor layer, and
 wherein the semiconductor layer includes a compound comprising a plurality of optionally substituted indolocarbazole moieties, which are the same or different from each other, wherein the covalent bonding between adjacent optionally substituted indolocarbazole moieties is a single covalant bond, wherein the indolocarbazole moieties are independently selected from the structures (A), (B), (C), (D), (E), (F) and (G), or a mixture thereof:

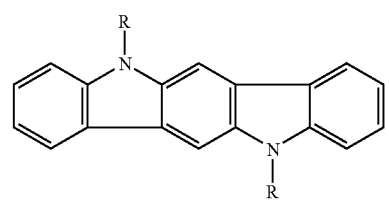

(A)

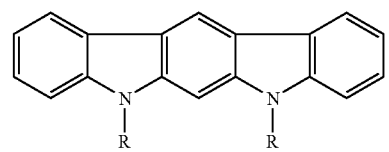

(B)

-continued (C)
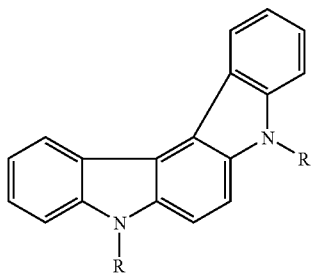

(D)
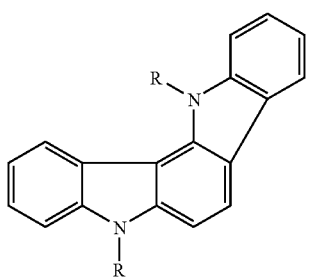

(E)
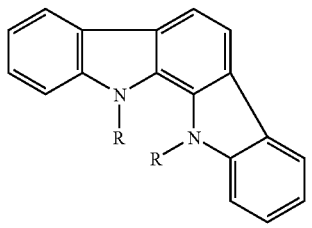

(F)
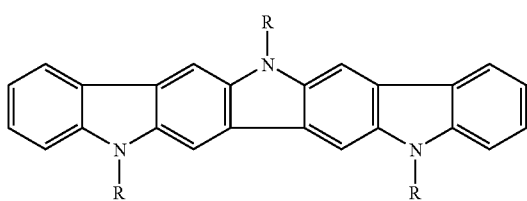

-continued (G)
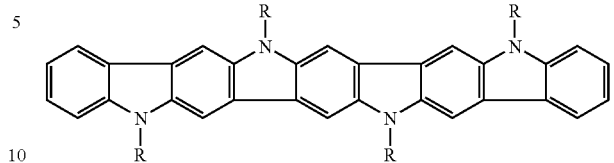

wherein for each of the structures (A) through (G), each R is independently selected from a group consisting of a hydrogen, a hydrocarbon group and a heteroatom-containing group, wherein each of the structures (A) through (G) is optionally peripherally substituted by a substituent selected from a group consisting of:

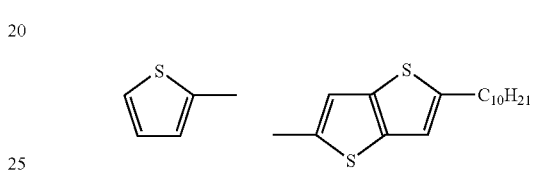

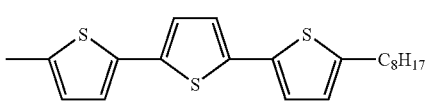

Cl, Br and —$C_8H_{17}$;

wherein the hydrocarbon group contains from 1 to 50 carbon atoms and is independently selected from a group consisting of: a straight chain alkyl group, a branched alkyl group, a cyclic aliphatic group, an aryl group, an alkylaryl group, and an arylalkyl group;

wherein the heteroatom-containing group contains from 2 to 200 atoms and is independently selected from a group consisting of: alkoxyaryl, arylalkoxy, fluoroalkyl, fluoroaryl, cyano, nitro, carbonyl, carboxylate, amino, alkoxy having 1 to 18 carbon atoms, and thienyl.

2. The transistor of claim 1, wherein the compound is selected from the group consisting of (1) through (10), or a mixture thereof:

(1)
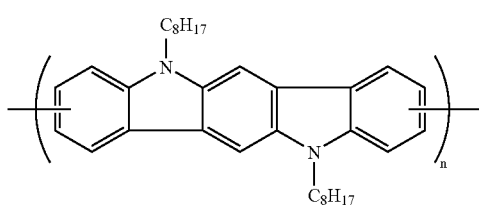

(2)
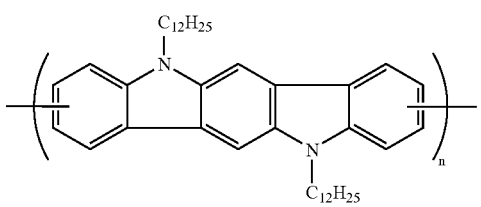

-continued
(3)
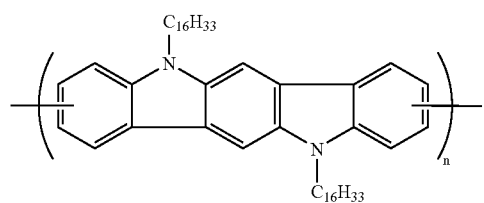
(4)
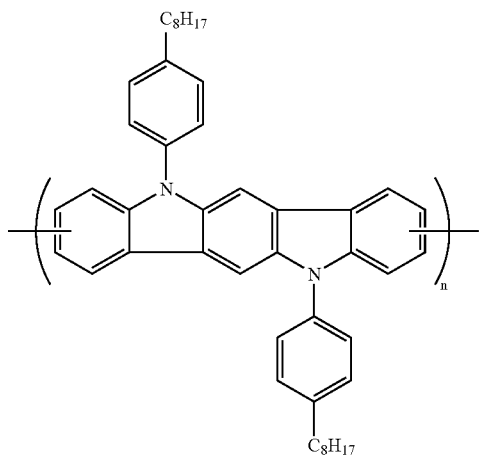
(5)
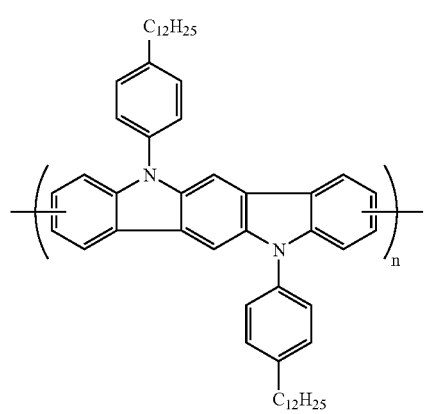
(6)
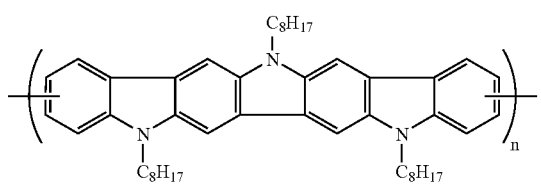
(7)
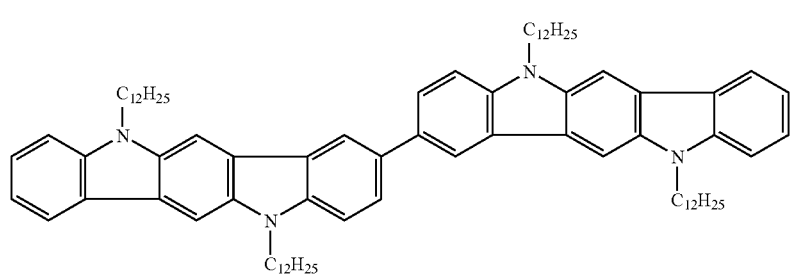
(8)
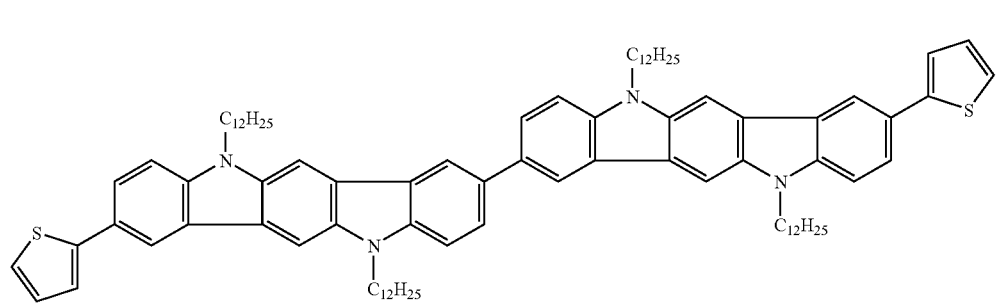

-continued

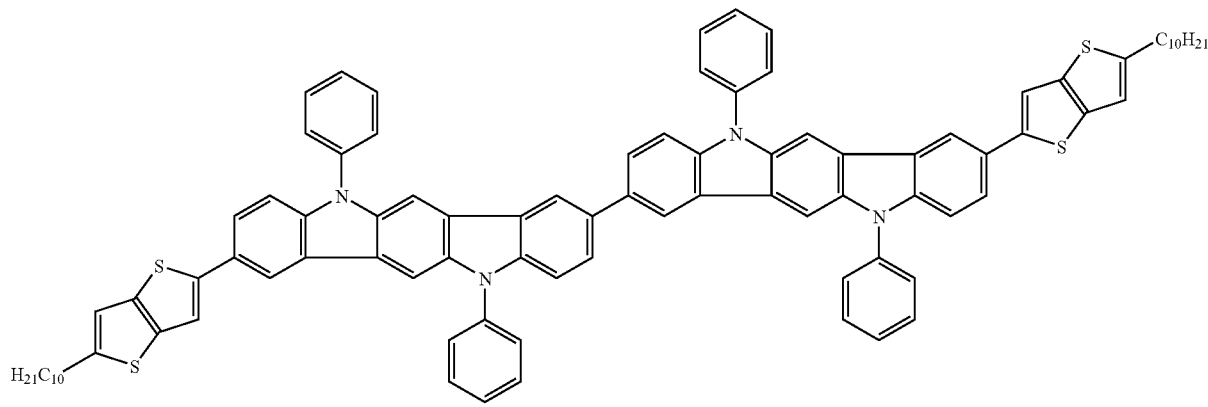

(9)

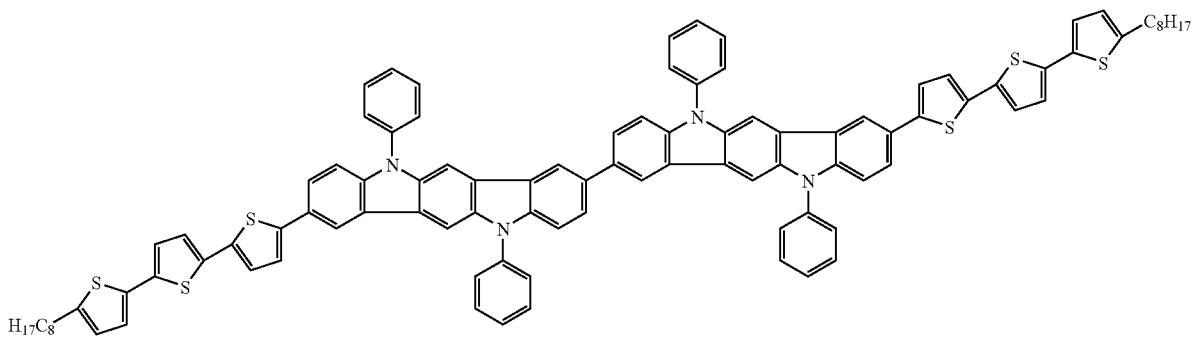

(10)

wherein n is an integer from 2 to 500.

3. The transistor of claim 1, wherein the compound has a band gap of greater than about 1.8 eV.

4. The transistor of claim 1, wherein the compound has a highest occupied molecular orbital energy level lower than about 4.9 eV from vacuum.

5. The transistor of claim 1, wherein the compound is substituted with at least one long chain alkyl to promote molecular self-assembly.

6. The transistor of claim 1, wherein the compound is substituted with one or more substituents independently selected from the group consisting of a long chain alkyl group, an alkylphenyl, a phenyl, a chloro, an alkoxy, an optionally substituted thienyl, and an optionally substituted amino, or a mixture thereof.

7. The transistor of claim 1, wherein the semiconductor layer is predominately crystalline.

* * * * *

UNITED STATES PATENT AND TRADEMARK OFFICE
CERTIFICATE OF CORRECTION

PATENT NO. : 7,402,681 B2
APPLICATION NO. : 11/167512
DATED : July 22, 2008
INVENTOR(S) : Beng S. Ong et al.

It is certified that error appears in the above-identified patent and that said Letters Patent is hereby corrected as shown below:

In the Specification

Column 1, line 27, please delete "70NANBOH3033" and insert --70NANB0H3033--.

Signed and Sealed this
Third Day of September, 2013

Teresa Stanek Rea
*Acting Director of the United States Patent and Trademark Office*